(12) United States Patent
Chadwick et al.

(10) Patent No.: US 6,387,686 B2
(45) Date of Patent: May 14, 2002

(54) METHODS AND COMPOSITIONS FOR IDENTIFYING A POLYNUCLEOTIDE ENCODING A PROTEASE

(75) Inventors: Mark P. Chadwick, Cambridge (GB); Stephen J. Russell, Rochester, MN (US); Christian Buchholz, Frankfurt (DE)

(73) Assignee: BioFocus Discovery Limited, Cambridge (GB)

( * ) Notice: Subject to any disclaimer, the term of this patent is extended or adjusted under 35 U.S.C. 154(b) by 0 days.

(21) Appl. No.: 09/791,427

(22) Filed: Feb. 23, 2001

Related U.S. Application Data

(60) Provisional application No. 60/184,982, filed on Feb. 25, 2000.

(51) Int. Cl.$^7$ .............................. C12N 7/00; C12Q 1/70; C12Q 1/68; C07H 21/04
(52) U.S. Cl. ............................ 435/235.1; 435/5; 435/6; 536/23.4; 536/23.72
(58) Field of Search ............................. 435/5, 6, 235.1; 536/23.4, 23.72

(56) References Cited

U.S. PATENT DOCUMENTS

| | | | |
|---|---|---|---|
| 5,324,634 A | 6/1994 | Zucker | 435/7.23 |
| 5,723,287 A | 3/1998 | Russell et al. | 435/5 |
| 5,998,192 A | 12/1999 | Russell et al. | 435/235.1 |
| 6,017,761 A | 1/2000 | Rigg et al. | 435/455 |
| 6,022,948 A | 2/2000 | Goldberg | 530/326 |

FOREIGN PATENT DOCUMENTS

| | | |
|---|---|---|
| WO | WO97/08194 | 8/1996 |

*Primary Examiner*—Hankyel T. Park
(74) *Attorney, Agent, or Firm*—Kathleen M. Williams; Palmer & Dodge, LLP

(57) ABSTRACT

Methods are disclosed whereby protease activity is directly linked to delivery of a transferable label to a target cell which expresses a protease, via fusion of viral display packages comprising the transferable label with the target cell. The methods can be used, inter alia, to identify proteases, including previously undiscovered proteases or variants of known proteases which may have altered substrate specificity.

51 Claims, 1 Drawing Sheet

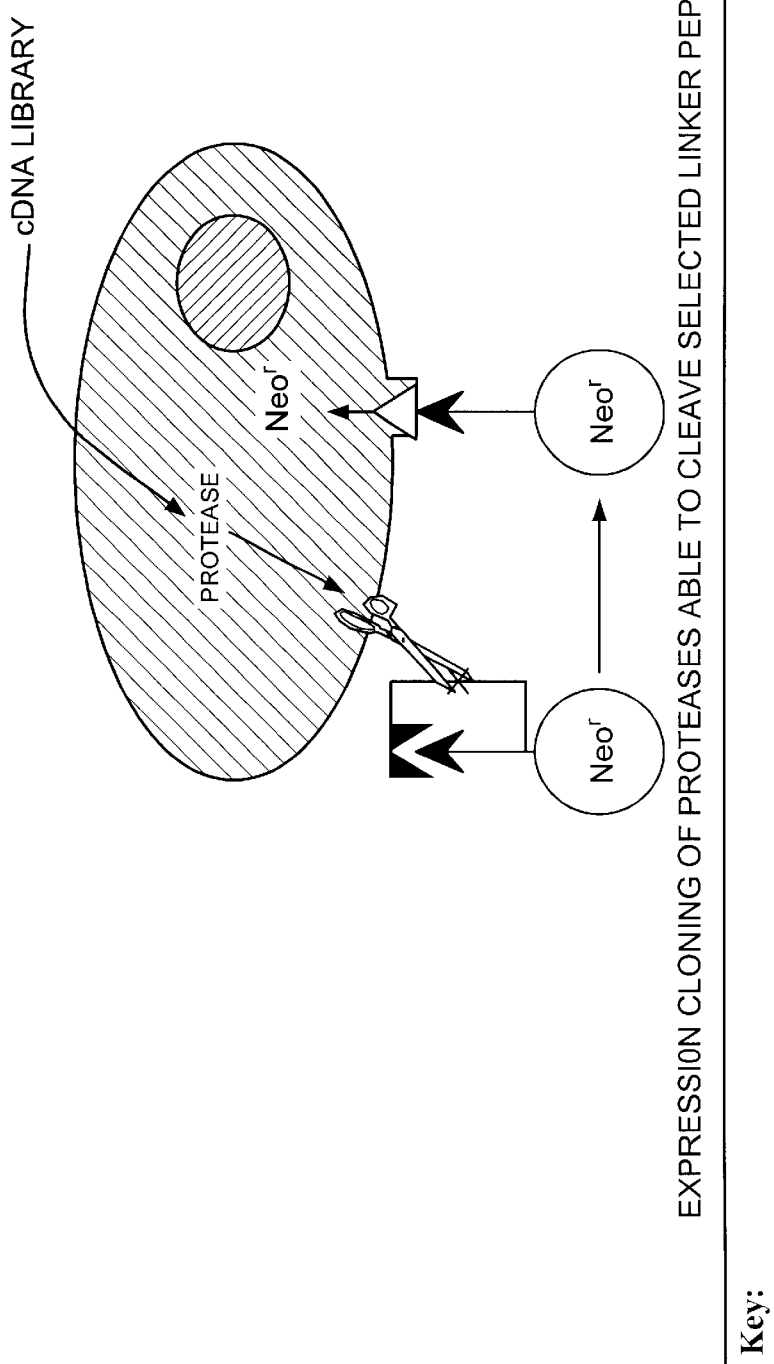

METHODS AND COMPOSITIONS FOR IDENTIFYING A POLYNUCLEOTIDE ENCODING A PROTEASE

This appln claims benefit of Prov. No. 60/184,982 filed Feb. 25, 2000.

TECHNICAL FIELD OF THE INVENTION

The invention relates to the identification and cloning of coding sequences for proteases, particularly novel proteases.

BACKGROUND OF THE INVENTION

Proteases are involved in a variety of cellular processes, such as tumor invasion, wound healing, tissue remodeling, infection, and inflammation. Previously unknown proteases whose substrate specificities are known can be used, for example, to design compounds which can affect these processes, including therapeutic compounds for conditions such as cancer, inflammation, rheumatoid arthritis and other autoimmune diseases, and AIDS.

Many methods are available in the art for detecting protease activity. For example, WO 97/08194 allegedly discloses a method of assaying for protease activity by measuring the fluorescence intensity of a fluorescent substrate. It would be advantageous to have a method in which detection of protease activity is linked to identification of a polynucleotide encoding the protease. Thus, there is a need in the art for convenient and rapid methods which can be used both for detection of protease activity and for identification of polynucleotides encoding the protease.

SUMMARY OF THE INVENTION

It is an object of the present invention to provide methods for identifying coding sequences for proteases which are expressed under a variety of conditions, including proteases which were previously unknown. This and other objects of the invention are provided by one or more of the embodiments described below.

One embodiment of the invention is a method of identifying a candidate polynucleotide molecule encoding a protease, such as a cell surface or a secreted protease. Viral display packages are contacted with target cells. The viral display packages comprise a transferable label and display a chimeric envelope protein comprising (I) a substantially intact viral envelope protein which enhances fusion between a viral display package and a target cell membrane, (ii) an inhibitory protein which prevents fusion between the viral display package and the target cell membrane, and (iii) a protease recognition site located between the substantially intact viral envelope protein and the inhibitory protein. In another embodiment, the viral display packages display recombinant envelope proteins, in which a protease recognition site has been substituted for a grin cleavage site located between a large glycoprotein subunit of the envelope protein and a transmembrane component of the envelope protein. Recombinant envelope proteins can be derived from viral envelope proteins such as a Moloney murine leukemia virus envelope protein or an influenza virus envelope protein.

A "protease recognition site" according to the invention is a contiguous sequence of amino acids connected by peptide bonds which are recognized by a protease. Recognition of this site by a protease results in cleavage (i.e., hydrolysis) of peptide bond by the protease. The site of hydrolysis may be coincident with the protease recognition site, that is, the protease recognition site may include one or more amino acids on either side of the peptide bond to be hydrolyzed which are recognized by the particular protease. The specific sequence of amino acids in the protease recognition site depends on the catalytic mechanism of the protease, which is defined by the nature of the functional group at the protease's active site. Alternatively, the protease recognition site may be one, two, three, four or more amino acids distal, at the amino or carboxy terminus, to the site of cleavage by the protease. If desired, the protease recognition site can be a variation of a recognition site of a known protease. Preferably, the variation of the known recognition site is formed by modifying at least one amino acid of the known protease recognition site.

Preferably, the substantially intact retroviral envelope protein is a murine leukemia virus envelope protein, such as a 4070A or Moloney murine leukemia virus envelope protein.

In one embodiment, the inhibitory protein binds to a receptor present on the outer cell membrane of the target cell. The inhibitory protein can be, for example, CD3 antigen, epidermal growth factor, stem cell factor, and an insulin-like growth factor I. In another embodiment, a first inhibitory protein oligomerizes with at least second inhibitory protein, such as CD40 ligand or a leucine zipper polypeptide, for example GCN4, C/EBP, Fos, Jun, and c-myc.

A transferable label can be any label whose presence can be detected in the target cell upon fusion of the viral display package and the target cell membrane Preferably, the transferable label is a gene encoding a selectable marker or is a reporter gene.

Target cells comprise(I) expressible candidate polynucleotide molecules, wherein the expressible candidate polynucleotide molecules may or may not encode a protease. The target cell can be a cell which is likely to express a protease, such as a tumor cell, a cell of a tissue which is inflamed, a cell of a tissue which is undergoing remodeling, a cell of a tissue which is involved in wound healing, or a cell comprising an infectious agent which expresses a protease. If desired, candidate polynucleotide molecules can be obtained from such cells and introduced into target cells. Candidate polynucleotides also can be obtained from cells which are known to express a protease or which are not known to express a protease. Optionally, candidate polynucleotides are synthetic polynucleotides or are polynucleotides which encode a mutated form of a known protease. Candidate polynucleotides can be obtained from a cDNA library.

Infection of a target cell by a viral display package comprising the transferable label preferably occurs only if a protease produced in the target cell removes the inhibitory protein from the chimeric envelope protein or, if a recombinant envelope protein is displayed, only if a protease produced in a member of the first plurality of target cells activates the envelope protein by cleaving it at the protease recognition site between the large glycoprotein subunit and the transmembrane component. Target cells may be treated with growth factors, activating proteases or other compounds to modulate the protease activity of the target cells, As used herein, the term "treatment to modulate protease activity" refers to a process or treatment that results in activation of a protease expressed in a zymogen or proenzyme form. This treatment may, for example, activate or even introduce a proteolytic enzyme required for cleavage of a zymogen form of a protease.

As used herein, the term "growth factor" refers to a polypeptide that alters protease activity in a cell through interaction of the polypeptide with a specific receptor expressed by that cell.

As used herein, the term "activating protease" refers to a proteolytic activity that, through cleavage of one or more polypeptides, modulates the activity of a cellular protease.

As used herein, the term "protease-modulating compound" refers to a compound that directly or indirectly activates a cellular protease. Detection of a target cell which comprises the transferable label thus indicates that the target cell expresses the protease.

Primers can be included in the candidate polynucleotide molecules, for use in amplifying a candidate polynucleotide molecule which encodes a protease. Amplified candidate polynucleotide molecules can then be sequenced to identify the encoded protease.

Thus, the present invention provides an innovative approach to the identification of protease coding sequences, including those which are novel or have altered substrate specificities.

BRIEF DESCRIPTION OF THE DRAWINGS

FIG. 1 is a schematic view of a method of cloning a protease-encoding polynucleotide. Protease negative cells identified in WP18 will be transfected with a cDNA library derived from protease positive cells. The cells will then be incubated with retroviral vector particles activatable by the protease to be cloned and which carry the neomycin resistance gene (neo). Cells that express a protease able to cleave the selected linker peptide at a specific substrate site will activate the vector particles and therefore become neomycin resistant.

DETAILED DESCRIPTION

It is a discovery of the present invention that the components described below can be assembled to provide a system in which protease activity is directly linked to transfer of a label from a viral display package to a target cell which expresses the protease. In one embodiment, viral display packages display a chimeric envelope protein. The chimeric envelope protein comprises (I) a substantially intact viral envelope protein which enhances fusion between a viral display package and a target cell membrane, (ii) an inhibitory protein which prevents fusion between the viral display package and the target cell membrane, and (iii) a protease recognition site located between the substantially intact viral envelope protein and the inhibitory protein. In another embodiment, viral display packages display a recombinant envelope protein, rather than a chimeric envelope protein. Envelope proteins comprise a large glycoprotein subunit (SU), which mediates attachment to a cellular receptor, and a smaller transmembrane component (TM), which is responsible for fusion between viral and cellular membranes separated by a furin cleavage site. Furin cleavage in the golgi apparatus activates the envelope protein, such that it can bind to its receptor on a target cell and mediate virus-cell fusion.

Recombinant envelope proteins of the invention are envelope proteins in which a protease recognition site according to the invention has been substituted for the furin cleavage site. In this case, a viral display package displaying a recombinant envelope protein is activated when a protease hydrolyzes a peptide bond in the protease recognition site to enable the transmembrane component to mediate fusion with the target cell membrane.

Target cells comprise expressible candidate polynucleotide molecules which may or may not encode a protease. The inhibitory protein impairs fusion of the viral display package with a target cell membrane unless the inhibitory protein is removed from the chimeric envelope protein by a specific protease which recognizes the protease recognition site and hydrolyzes a particular peptide bond within the site. If a target cell expresses a protease that can hydrolyze the peptide bond, then a viral display package which displays the cleaved chimeric envelope protein can deliver its transferable label to the target cell. The presence of the transferable label in a target cell identifies that cell as expressing a protease. The candidate polynucleotide molecule encoding the protease can then be isolated from the target cell using well-known methods. For example, PCR or other amplification methods can be used to amplify the candidate polynucleotide, using primers specific to regions upstream and downstream of the candidate polynucleotide. The amino acid sequence of the encoded protease can be determined by sequencing the amplified products.

This discovery permits the discovery of new proteases, whether they are previously undiscovered proteases or amino acid sequence variants of previously known proteases having altered substrate specificity, by identifying a polynucleotide molecule encoding a new protease. Thus, cloning of a protease-encoding polynucleotide according to the invention can be achieved when the cleavage site of the unknown protease is known. Once the polynucleotide is identified and cloned, the amino acid sequence of the encoded protease can be deduced and the protease identified. This method is particularly useful, for example, when it is discovered that an extracellular portion of a receptor is shed from the cell surface by the action of an unknown protease. In addition, proteases with altered or novel substrate specificities can be detected, using candidate polynucleotides which encode known proteases in which the active site has been altered and assaying the encoded proteases for the ability to cleave a protease recognition site which has also been altered. Such proteases can be used to degrade proteins which are overexpressed in diseases such as Alzheimer's disease or cancer, or for removing a pathogenic organism attached by means of a peptide bond to a cell surface receptor, such as a receptor present on the respiratory lining. Identified proteases can also be used for agricultural purposes, for example to degrade essential proteins of a pest on a crop, particularly a commercial crop.

A particular advantage of the present invention is that protease so identified is identified in a physiological environment and therefore is active in a physiological environment. The identified proteases can be used, for example, to screen for inhibitors of the protease which can be used therapeutically, for treating conditions such as cancer, rheumatoid arthritis or other autoimmune diseases, inflammation, or infections such as AIDS, herpes, or hepatitis.

Proteases Identifiable According to the Invention

A "protease" which can be identified according to the invention is an enzyme which hydrolyzes a peptide bond between a pair of amino acids located in a polypeptide chain, also called an endoprotease. Proteases are typically defined by reference to the nucleophile in the catalytic center of the enzyme. The most common nucleophiles arise from the side chains of serine, aspartic acid, and cysteine, resulting in families of proteases, such as serine proteases (Paetzel et al., *Trends Biochem. Sci.* 22, 28–31, 1997), aspartyl proteases (Spinelli et al., *Biochemie* 73, 1391–96, 1991), and cysteine proteases (Altschuh et al., *Prot. Eng.* 7, 769–75, 1994). Metalloproteases usually contain a zinc catalytic metal ion at the catalytic site (Klimpel et al., 1994, *Mol. Microbiol.* 13, 1093–100). Examples of members of each of these protease families are provided in Table I.

TABLE I

Proteases and Protease Recognition Sites (* indicates the peptide bond being hydrolyzed)

| Protease Family | Protease | Protease Recognition Sites |
| --- | --- | --- |
| serine | factor Xa | Ile-Glu-Gly-Arg* |
| serine | trypsin | Lys*, Arg* |
| serine | chymotiypsin | Tyr*, Phe*, Leu*, Ile*, Val*, Trp*, and His* at high pH |
| serine | thrombin | Arg* |
| serine and cysteine variants | peanut mottle polyvirus NIa protease | Glu-Xaa-Xaa-Tyr-Xaa-Gln*(Ser/Gly) |
| cysteine | papain | Arg*, Lys*, Phe* |
| cysteine | bromelain | Lys*, Ala*, Tyr*, Gly* |
| cysteine | cathepsin B | Arg*Arg, Phe*Arg |
| cysteine | cathepsin L | Phe*Arg |
| aspartyl | HIV protease | Phe*Pro |
| aspartyl | S. cerevisiae yapsin 2 | Lys*, Arg* |
| aspartyl | cathepsin D | phe*Phe, Phe*Lys, Leu*Phe, Leu*Tyr |
| metallo- | thermolysin | *Tyr, *Phe, *Leu, *Ile, *Val, *Trp, and *His |
| metallo- | peptidyl-Lys metalloendopeptidase | Xaa*Lys |
| metallo- | peptidyl-Asp metalloendopeptidase | Xaa*Asp, Xaa*Glu, Xaa*Cys |
| metallo- | coccolysin | *Leu, *Phe, *Tyr, *Ala |
| metallo- | autolysin | Leu-Trp-Met*Arg-Phe-Ala |
| metallo- | human neutrophil collagenase (MMP-8) | Gly-Leu-Ser-Ser-Asn-Pro*Ile-Gln-Pro |
| metallo- | gelatinase A (MMP-2) | Pro-Gln-Gly*-Ile-Ala-Gly-Gln |

Protease Recognition Sites

A "protease recognition site" according to the invention is a contiguous sequence of amino acids connected by peptide bonds which contains (I) a pair of amino acids which is connected by a peptide bond that is hydrolyzed by a particular protease. Optionally, a protease recognition site according to the invention may include one or more amino acids on either side of the peptide bond to be hydrolyzed, to which the catalytic site of the protease also binds (Schecter and Berger, Biochem. Biophys. Res. Commun. 27, 157–62, 1967), or the recognition site and cleavage site on the protease substrate may be two different sites that are separated by one or more (e.g., two to four) amino acids. If the protease recognition and cleavage sites are distinct sites on the protease substrate, then the recognition sites is positioned between the substantially intact viral envelope protein and the inhibitory domain in the chimeric envelope protein, and the cleavage site is present on one or the other side of the recognition site such that cleavage removes the inhibitory domain to permit infection of the second plurality of target cells by the viral package. That is, cleavage should not interfere with the ability of the substantially intact viral envelope protein to enhance fusion with the target all membrane and proceed with infection.

The specific sequence of amino acids in the protease recognition site depends on the catalytic mechanism of the protease, which is defined by the nature of the functional group at the protease's active site, as discussed above. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg and hydrolyzes peptide bonds on the C-terminal side of the Arg.

Thus, a protease recognition site comprises at least 2, 3, 4, 5, 6, 7, 8, 9, or 10 or more amino acids. Optionally, additional amino acids can be present at the N-terminus and/or C-terminus of the recognition site. A protease recognition site according to the invention also can be a variant of a recognition site of a known protease, such as the protease recognition sites shown in Table I, above.

Optionally, a protease recognition site can be selected using a method such as that taught in U.S. Pat. No. 5,780,279. This method involves producing a fusion gene encoding a polypeptide, a substrate peptide, and at least a portion of a phage coat protein. The DNA encoding the substrate peptide is mutated at one or more codons to generate a family of mutants. The mutant fusion proteins are expressed on the surface of a phagemid particle and then exposed to a protease which may or may not recognize and cleave the mutant substrate peptide. If cleavage does occur, the polypeptide will become dissociated from the phagemid particle, and when the phagemid particle is contacted with an affinity molecule specific for the polypeptide, it will not bind. Thus, phagemid particles which express mutant fusion proteins comprising a substrate peptide which can be cleaved by a protease can be separated from those which do not express such fusion proteins. The substrate peptide so identified can be used to provide a protease recognition site for use in methods of the invention.

Viral Display Packages

Viral display packages are well known in the art (see, e.g. U.S. Pat. No. 5,723,287). Viral display packages of the invention display chimeric envelope proteins on their surface. Production of such viral display packages is taught, for example, in U.S. Pat. No. 5,723,287, and in Chadwick et al., 1999. Briefly, viral packaging cells, such as Psi 2, TELCeB.6, and PA317, are conveniently used to produce viral display packages. The packaging cells comprise a transferable labels which is packaged into viral display particles. The packaging cells also comprise a nucleic acid molecule with a coding sequence for a chimeric envelope protein.

Chimeric Envelope Proteins

A "chimeric envelope protein" comprises the following three components from N- to C-terminus: (1) an inhibitory protein, which is capable of impairing the function of the envelope protein and hence fusion of the envelope protein with its target cell membrane, (2) a protease recognition site, and (3) a substantially intact viral envelope protein which mediates fusion between the viral display package and the target cell membrane ,i.e. enhances fusion above the level of fusion which occurs in the absence of the substantially intact viral envelope protein.

Nucleic acid molecules encoding chimeric envelope proteins can be produced using recombinant DNA technology or can be synthesized using standard nucleic acid synthesis techniques. Envelope proteins of adenovirus, togavirus, rhabdovirus, and retrovirus families, as well as from enveloped viruses such as paramyxovirus and orthomyxovirus, are useful in the chimeric envelope protein. Murine leukemia virus envelope proteins, such as the 4070A and Moloney MLV envelope proteins, are particularly useful for this purpose.

1. Viral Envelope Proteins

It is important that the viral envelope protein is substantially intact, i.e. retains all its domains, to conserve post-translational processing, oligomerization, viral incorporation, and fusogenic activities. However, certain alterations, such as mutations, deletions, or additions, can be made to the viral envelope protein which do not significantly affect these functions, and viral envelope proteins with such modifications are considered substantially intact. It is not necessary that an entire viral envelope protein be used, but the portion of the viral envelope protein included in the chimeric envelope protein must be able to mediate fusion between the viral display package and the outer cellular membrane of the target cell.

2. Inhibitor Proteins

An "inhibitory protein" useful in the chimeric envelope protein is a protein or a portion of a protein which prevents the substantially intact viral envelope protein from mediating fusion of the viral display package with the cell membrane of a target cell. At least two types of inhibitory proteins are useful in the chimeric envelope protein.

One type of inhibitory protein binds to a receptor on the target cell. This type of inhibitory protein thus may include, but is not limited to, a single-chain antibody fragment to a hapten (Russell et al., *Nucleic Acids Research* 21(5), 1081–1085, 1993), CD3 or colonic carcinoma cell antigens (Ager et al., *Human Gene Therapy* 7(17), 2157–2164, 1996), or a cellular growth factors such as epidermal growth factor (EGF, Cosset et al., *Journal of Virology* 69(10), 6314–6322, 1995), stem cell factor (SCF, Fielding et al., *Blood* 91(5), 1802–9, 1998), and insulin-like growth factor I (IGF-I, Chadwick et al., *J Mol Biol* 285(2), 485–94, 1999).

Amino acid sequences of such inhibitory proteins, as well as nucleotide sequences encoding them, are available in the scientific literature and in databases such as GenBank. For example, the nucleotide sequence encoding the 53 amino acids of EGF can be obtained from a cDNA template (ATCC 59957) using primers disclosed in Cosset et al. (1995). Primers for amplifying a cDNA sequence encoding SCF (e.g., GenBank Accession No. U80930.1) are disclosed in Fielding et al. (1998). Primers for amplifying IGF-I cDNA (GenBank Accession No. M37484) are disclosed in Chadwick et al. (1999). Alternate nucleotide sequences which encode these inhibitory proteins also can be synthesized and used to produce an inhibitory protein.

A receptor for an inhibitory protein can be present naturally on the target cell membrane or can be introduced into the target cell such that it is expressed as a heterologous receptor on the cell surface using standard molecular biological techniques. For example, the nucleotide sequence encoding the type-1 IGF receptor is disclosed in Ullrich et al., *EMBO J.* 5(100), 2503–12 (1986) and in GenBank Accession No. X04434 M 24599. The nucleotide sequence encoding the EGF receptor is disclosed in Ullhrich et al., *Nature* 309(5967) 418–25 (1984) and in GenBank Accession No. X00588. Yarden et al., *EMBO J.* 6(11), 3341–51 (1987), and GenBank Accession No. X06182 disclose the coding sequence for the SCF receptor.

Another type of inhibitory protein oligomerizes with at least one, preferably two other inhibitory proteins of the same type in other chimeric envelope proteins. This type of inhibitory protein includes trimeric polypeptides such as the C-terminal extracellular domain of CD40 ligand (Karpusas et al., 1995, *Structure* 3, 1031–39), as well as leucine zipper polypeptides (Harbury et al., 1993, *Science* 262, 1401–07). Leucine zipper polypeptides according to the invention characteristically possess two domains—a leucine zipper structural domain and a basic domain that is rich in basic amino acids (Vinson et al., 1989, *Science*, 246, 911–916). The two domains are separated by a short segment known as the fork. Leucine zipper polypeptides include the yeast transcription factor GCN4, the mammalian transcription factor CCAAT/enhancer-binding protein C/EBP (Landschulz et al., *Science* 243, 1681, 1989), the nuclear transforming oncogene products Fos and Jun (O'Shea et al., *Science* 245, 646, 1989; Turner and Tjian, *Science* 243, 1689, 1989), and the gene product of the murine proto-oncogene, c-myc (Landschulz et al., *Science* 240, 1759, 1988). Preparation of 4070A and Moloney MLV envelope proteins comprising such inhibitory proteins is disclosed in Morling et al., *Virology* 234(1), 51–61, 1997.

An inhibitory protein may be a full-length protein or it may be that portion of the protein that either oligomerizes or binds to the corresponding receptor present on the target cell membrane. It is well known that amino acids of a protein which binds to a receptor can be deleted without affecting the receptor-binding portion of the protein. For example, U.S. Pat. No. 5,859,208 discloses alterations which can be made to fibroblast growth factor without affecting its receptor binding domain. Similarly, U.S. Pat. No. 5,849,689 discloses alterations which can be made to hepatocyte growth factor. Leucine zipper polypeptides can also be modified without affecting their ability to oligomerize (see van Heeckeren et al., 1992, *Nucleic Acids Res.* 20,3721–24). Portions of inhibitory proteins can be screened for the ability to prevent delivery of the contents of a viral display package using routine screening methods. For example, a portion of an inhibitory protein can be included in a chimeric envelope protein and tested for the ability to block gene transfer or transfer of a label, as described in Cosset et al., 1995 (*J. Virol.* 69, 6314–22).

Mechanism of Action

Without being bound to any particular mechanism of action, an inhibitory protein which binds to a receptor on the target cell is believed to prevent delivery of the contents of the viral display package to the target cell by receptor-mediated sequestration. Receptor-mediated sequestration occurs when receptors for an inhibitory protein are present on the surface of the target cell. Binding of the chimeric envelope protein to a cell surface receptor by means of the inhibitory protein of the chimeric envelope protein sequesters the viral display package and thus prevents it from binding a viral envelope protein receptor on the cell surface. Thus, the viral display package cannot bind to the viral receptor on the cell surface or fuse to the cell membrane and transfer a label (such as a gene).

Similarly, without being bound to any particular mechanism of action, it is believed that an inhibitory protein which oligomerizes impairs gene delivery by formation of an oligomeric cap on a viral glycoprotein (WO 90/04562; Morling et al., *Virology* 234(1), 51–61, 1997). The oligomeric cap forms by intermolecular association between heterologous inhibitory proteins displayed on different chimeric envelope proteins. The intermolecular association may be via non-covalent bonds or via covalent bonds, such as disulfide bonds. For example, the C-terminal extracellular domain of CD40 ligand forms such an oligomeric cap when displayed on a trimeric chimeric envelope protein. CD40 ligand is a homotrimer and therefore exhibits the same stoichiometry of association as the envelope glycoprotein itself. CD40 ligand displays significantly reduced envelope-protein mediated transfer to target cells by inhibiting binding of the envelope protein to its receptor and likely also by inhibiting subsequent fusion triggering, which requires the dissociation of a trimeric envelope protein into its subunits. Display of trimeric leucine zipper polypeptides produces a similar phenotype via the formation of an oligomeric cap (Morling et al., 1997).

Recombinant Envelope Proteins

A "recombinant envelope protein" of the invention is derived from any viral envelope protein which comprises a large glycoprotein subunit which is capable of binding to a cognate viral envelope receptor on the surface of the target cell, a furin cleavage site, and a transmembrane component which mediates fusion between the viral membrane and the membrane of the target cell. In a recombinant envelope protein of the invention, a protease recognition site has been substituted for the furin cleavage site, at the same position in the envelope protein. Envelope proteins such as the envelope proteins of Moloney murine leukemia virus, 4070A, or influenza virus, can be used to derive a recombinant envelope protein. If a Moloney murine leukemia virus is used, the protease recognition site is located between the large glycoprotein subunit (SU) and the transmembrane component (TM). If an influenza virus envelope protein is used, the protease recognition site is located between the HA1 and HA2 portions of the envelope protein. Such recombinant envelope proteins can be constructed using standard molecular biology techniques, to delete the furin cleavage site of an envelope protein and substitute a desired protease recognition site.

Transferable Labels

Viral display packages also comprise a "transferable label" for identification and/or selection of target cells which have been infected by a viral display package. A transferable label can be any label whose presence can be detected in the target cell upon fusion of the viral display package and the target cell membrane Preferably, the transferable label is a gene encoding a selectable marker or a reporter gene.

Genes encoding selectable markers are preferably antibiotic-resistance genes, such as a neomycin, puromycin, or pleomycin resistance gene. Reporter genes encode a detectable product, such as β-galactosidase, luciferase, β-glucuronidase, green fluorescent protein (GFP), autofluorescent proteins, including blue fluorescent protein (BFP), glutathione-S-transferase (GST), luciferase, horseradish peroxidase (HRP), or chloramphenicol acetyltransferase (CAT). Many such genes are known in the art. Transferable labels also include proteins which can be detected using immmunochemical techniques employing antibodies which specifically bind to the protein product.

Polynucleotides encoding selectable markers or reporter gene products can be transfected into target cells as described above, for subsequent packaging into viral display packages. Alternatively, an antibiotic resistance gene or reporter gene can be included in a candidate polynucleotide, either up- or downstream from the open reading frame of the candidate polynucleotide.

Candidate Polynucleotides

A "candidate polynucleotide" according to the invention comprises a coding sequence for a protein, including a protease. The term "candidate polynucleotide" encompasses a single candidate polynucleotide molecule or a plurality of two or more of such molecules, ideally representing a population of (e.g., 5,000 to 10,000, 10,000 to 20,000, 20,000 to 30,000, 30,000 to 50,000, 50,000 to 100,000, or $10^6$ or $10^7$) of such polynucleotides to be screened according to the invention.

Candidate polynucleotides contain less than a whole chromosome and can be RNA or single- or double-stranded genomic or cDNA. Preferably the polynucleotides are isolated free of other cellular components, such as membrane components, proteins, and lipids. They can be made by a cell and isolated, or synthesized in the laboratory using an amplification method such as PCR or using an automatic synthesizer. Methods for purifying and isolating DNA are routine and are known in the art (for example, see Sambrook et al., MOLECULAR CLONING, 2d ed., 1989; Perbal, A PRACTICAL GUIDE TO MOLECULAR CLONING, 2d ed., 1988).

Candidate polynucleotides can be obtained from a cell which is not known to express a protease, from a cell which is known to express a protease, or from a cell which is likely to express a protease. Cells which are likely to express proteases are obtained, for example, from tissues which are known to produce substantial proteolysis, such as a tumor, a tissue which is inflamed, a tissue which is undergoing remodeling, such as a developing limb bud, or a tissue which is involved in wound healing. Cells comprising a pathogen, such as an HIV virus, a rhinovirus, a herpes viruses, a hepatitis virus, or other infectious agent which express proteases, also can provide candidate polynucleotides. Cells which express proteases can be identified, for example, using protease assays employing substrates which produce a detectable product, such as a chromogenic or fluorescent substrate. Substrates and protease assay kits are commercially available from companies such as Molecular Probes, Inc., Promega, and CLONTECH.

Candidate polynucleotides can be present in plasmids of a cDNA expression library, which cDNA library can be constructed from cells known to express a protease. Ideally, the cDNA expression library will include a population of plasmids, where each plasmid contains an expression cassette comprising a candidate polynucleotide operatively linked to a promoter such that the open reading frame in the candidate polynucleotide is expressed. Methods of preparing cDNA and of constructing cDNA expression libraries are well known in the art, and any such methods can be used (see Sambrook et al., 1989; Perbal et al., 1988). Suitable plasmids can be constructed using standard recombinant DNA techniques or can be purchased from commercial suppliers.

In another embodiment of the invention, candidate polynucleotides encode variations of a known protease molecule. Polynucleotides encoding any known protease can be varied, including but not limited to members of the serine protease, aspartyl protease, cysteine protease, and metalloprotease families mentioned above. Preferably, amino acids involved in the recognition active site of the amino acid substrate of the known protease are varied.

Polynucleotides encoding proteases can be obtained, for example, from cells such as those mentioned above, or can be produced recombinantly or synthetically. The polynucleotides can then be mutated, either randomly or at specific sites, to produce polynucleotides encoding variations of known protease sequences which have altered substrate specificity. Site-specific mutagenesis is taught, for example, in Watkins et al., *Biotechniques* 15,700–704 (1993), Weiner et al., *Gene* 126, 35–41 (1993), and Weiner et al., *Gene* 151,119–123 (1994). Optionally, polynucleotides encoding particular protease variations can be synthesized directly.

Preferably, candidate polynucleotides contain a selectable marker to facilitate subsequent selection of transfected target cells. Antibiotic resistance genes, such as a neomycin, puromycin, or phleomycin resistance gene, are particularly useful for this purpose.

Expression Cassettes According to the Invention

An "expression cassette" according to the invention is a polynucleotide construct which is capable of expressing a candidate polynucleotide molecule. Expression cassettes can be constructed using standard recombinant DNA techniques. Preferably, an expression cassette includes a candidate polynucleotide and a promoter. A variety of effective promoters, such as the CMV and β-actin promoters, are known in the art and can be operatively linked to the candidate polynucleotide molecules. Of course, the promoter must be selected to be operative in the particular target cell which is used in the method. Selection of appropriate promoters is well within the skill in the art.

Other sequences can be included in an expression cassette. For example, primer sequences can be included, for use in amplifying the candidate polynucleotide molecules. Endoplasmic reticulum and/or Golgi retention/retrieval signals also can be included so that the encoded protease will be retained in the export pathway of the target cell (Nilsson & Warren, *Curr. Opin. Cell Bid.* 6(4), 517–21 1994). If integration into the genome of the target cell is desired, expression cassettes can include sequences which permit such integration, such as viral long-terminal repeats (LTRs). Examples of LTRs include the LTR of the Rous sarcoma virus (Gorman et al., 1982, *Proc. Natl. Acad. Sci. U.S.A.* 79, 6777) the human cytomegalovirus LTR (Boshart et al., 1985, *Cell* 41, 521), and the Moloney MLV LTR (Van Beveren et al., 1980, *Proc. Natl. Acad. Sci. U.S.A.* 77(8), 3307–11).

Target Cells Useful in the Invention

Target cells can be cells which express a protease, such as those disclosed above, or can comprise expressible candidate polynucleotides, some of which may express a protease. If viral display packages which display a chimeric envelope protein are used, target cells should express on their surface a receptor for the substantially intact viral envelope protein used in the chimeric envelope protein. For example, if a Moloney murine leukemia virus envelope protein is used in the chimeric envelope protein, target cells should express the ecotropic CAT-1 receptor (Kavanaugh et al., 1991, *Nature* 352, 729–31). Similarly, if the 4070A murine leukemia virus protein is used, target cells should express the amphotropic Pit-2/Ram-1 receptor (Miller et al., 1994, *Proc. Natl. Acad. Sci. U.S.A.* 91 (1), 78–82). The receptors can be expressed naturally by the target cells, or polynucleotides encoding the receptors can be introduced into target cells, as described below. Target cells also may express a receptor for an inhibitory protein, as discussed above.

If viral display packages which display a recombinant envelope protein are used, target cells should express on their surface a receptor for the envelope protein from which the recombinant envelope protein was derived. Thus, if the recombinant envelope protein is derived from a Moloney murine leukemia virus envelope protein, target cells should express CAT-1. If the recombinant envelope protein is derived from an influenza virus, target cells should express a sialic acid receptor for the influenza virus envelope protein (Higa et al., 1985, *Virology* 144, 279–82). Some naturally-occurring proteases are expressed as zymogens—inactive forms of the protease that must be activated to express protease activity. Activation of the zymogen or "pro" form of a protease may occur, for example, through exposure to metal ions or through cleavage by a separate activating protease. When a protease is naturally expressed as a pro-form, the cDNA encoding the protease will encode the pro-form, rather than the active form. However, a number of proteases expressed in pro-form are activatable to a measurable extent by ubiquitous (e.g., furin-like) proteases present in target cells in addition to being activatable by cell-type specific proteases (Okumura et al., 1997, *FEBS Lett.* 402: 181–4; Sato et al., 1996, *FEBS Lett.* 393: 101–4; Pei & Weiss, 1995, *Nature* 375: 244–7). Further, target cells may be treated to activate the necessary proteolytic activity (ies) to allow activation of pro-form proteases in the methods of the invention. For example, growth factors, activating proteases or other protease-modulating compounds may be used to modulate protease activity in target cells (Campbell et al., 1994, *J Cell Physiol* 159: 1–10; Harano & Mizuno, 1994, *J Biol Chem* 269: 20305–11).

Transfection of Polynucleotides into Target Cells

Any appropriate method can be used to transfect polynucleotides into target cells. Methods of transfecting polynucleotides into cells are well known and include, but are not limited to, DEAE- and calcium phosphate-mediated transfection and electroporation. Variations of the calcium phosphate method appropriate for adherent cells, adherent cells released from the substratum with trypsin, and nonadherent cells are described in detail in Sambrook et al. (1989), at pages 16.32–16.40. Lipid compositions, such as Superfect by QIAGEN, can also be used for transfections.

The above disclosure generally describes the present invention, and all references cited in this disclosure are incorporated by reference herein. A more complete understanding of the invention can be obtained by reference to the following specific examples which are provided for purposes of illustration only and are not intended to limit the scope of the invention.

EXAMPLE 1

This example demonstrates the utility of the invention for cloning of an unknown protease when the protease substrate sequence is known. For illustrative purposes, the cloning of the metalloproteinase, MT1-MMP, is described.

Viral display packages comprising a neomycin resistance gene and displaying a chimeric envelope protein are produced from packaging cells which are generated from TE671 cells (ATCC CRL-8805). To generate the packaging cells, TE671 cells are transfected with a packaging-competent neomycin resistance gene and with packaging-defective plasmids encoding retroviral Gag and Pol polypeptides and a chimeric envelope protein. The chimeric envelope protein comprises, from N- to C-terminus, (1) 146 amino acids of the C-terminal domain of CD40L (residues 116–261), (2) Pro-Leu-Gly*-Leu-Trp-Ala, a cleavage site sequence for MT1-MMP, where * indicates the point of cleavage, and (3) a complete 4070A murine leukemia virus envelope protein. The packaging-defective plasmid encoding the chimeric envelope protein also includes a phleomycin resistance gene.

Packaging cells which produce viral display packages are selected by culturing the packaging cells in the presence of phleomycin. Viral display packages produced by the packaging cells are harvested by collecting supernatant from the packaging cells. The supernatant is filtered through a 0.45 µm filter and added to a culture of TE671 cells (target cells) which have been transfected with a cDNA expression library derived from RNA isolated from the fibrosarcoma cell line HT-1080 (ATCC Accession No. CCL-121) by superfection (QIAGEN). The cDNA expression library contains plasmids which contain cDNA molecules obtained from HT-1080 RNA, under the control of a CMV promoter. The plasmids also contain retroviral long-terminal repeats and primers for amplifying the cDNA molecules.

The viral display packages are then placed in contact with the TE671 target cells, which are subsequently incubated in the presence of neomycin to select for TE671 cells which have become neomycin resistant because they express a protease able to cleave the MT1-MMP recognition site in the chimeric envelope protein and thus activate the viral display particles.

cDNA molecules which were integrated into the genome of neomycin-resistant TE671 target cells are amplified by PCR, using primers complementary to sequences of the plasmid up- and downstream from the integrated cDNA molecules. The amplified DNA is then cleaved at the insertion sites for the cDNA molecules, and the sizes of the amplified products are determined on an agarose gel.

The major product on the agarose gel, containing a coding sequence for a protease which cleaved the MT1-MMP protease recognition site in the chimeric envelope protein, is sequenced using the dideoxynucleotide chain termination method (Sanger et al, *Proc. Natl. Acad. Sci. U.S.A.* 74, 5463, 1977). After sequencing, the predicted amino acid sequence of the identified protease is confirmed as that of MT1-MMP.

EXAMPLE 2

This example describes cloning of a gelatinase A (MMP-2)-related protease with an altered substrate specificity.

Point mutuations are introduced into double-stranded MMP-2 cDNA molecules by incorporating into separate pools of the double-stranded DNA each of the four α-thiophosphate dNTPs (Shortle et al., *Proc. Natl. Acad. Sci. U.S.A.* 79, 1588, 1982; Shortle & Lin, *Genetics* 110, 539, 1985). The pools of mutated cDNA molecules are then combined and inserted into plasmids to form a cDNA expression library. The plasmids also contain a retroviral long-terminal repeat and primers for amplifying the cDNA molecules. The plasmids are then transfected into cells which are negative for MMP-2 and unable to cleave the altered substrate sequence, e.g., TE671 cells, by superfection (QIAGEN).

The transfected TE671 cells are incubated with viral display packages comprising a neomycin resistance gene in the presence of neomycin, as described above. The viral display packages are produced as described in Example 1, except that they display a recombinant envelope protein comprising (1) the large glycoprotein subunit (SU) of a Moloney murine leukemia virus, (2) Pro-Gln-Gly-Ile-Tyr-Gly-Gln, a recognition site for MMP-2 in which Tyr has been substituted for Ala at the fifth position, and (3) a transmembrane subunit (TM) of a Moloney murine leukemia virus.

cDNA molecules which were integrated into the genome of neomycin-resistant TE671 cells are amplified by PCR, using primers complementary to sequences of the plasmid up- and downstream from the intergrated cDNA molecules. The amplified DNA is then cleaved at the insertion sites for the cDNA molecules, and the sizes of the amplified products are determined on an agarose gel.

The major product on the agarose gel, containing a coding sequence for a protease which cleaved the modified protease recognition site in the chimeric envelope protein is sequenced using the dideoxynucleotide chain termination method (Sanger et al., 1977). After sequencing, the predicted amino acid sequence of the identified protease is determined.

What is claimed is:

1. A method of identifying a candidate polynucleotide molecule encoding a cell surface protease or a secreted protease, comprising the steps of:
    (a) contacting viral display packages with target cells, wherein:
        (1) the viral display packages comprise a transferable label and display a chimeric envelope protein comprising (i) a substantially intact viral envelope protein which enhances fusion between a viral display package and a target cell membrane, (ii) an inhibitory protein which prevents fusion between the viral display package and the target cell membrane, and (iii) a protease recognition site located between the substantially intact viral envelope protein and the inhibitory protein; and
        (2) the target cells comprise expressible candidate polynucleotide molecules, wherein the expressible candidate polynucleotide molecules may or may not encode a protease; and
    (b) detecting a target cell which comprises the transferable label, wherein infection of a target cell by a viral display package occurs only if a protease produced in the target cell removes the inhibitory protein from the chimeric envelope protein.

2. The method of claim 1 further comprising the step of introducing a plurality of candidate polynucleotides into a population of target cells, wherein the plurality of candidate polynucleotides comprises candidate polynucleotide molecules expressible in the target cells.

3. The method of claim 1 wherein the chimeric envelope protein comprises a substantially intact retroviral envelope protein.

4. The method of claim 3 wherein the substantially intact retroviral envelope protein is a murine leukemia virus envelope protein.

5. The method of claim 4 wherein the murine leukemia virus envelope protein is obtained from a murine leukemia virus selected from the group consisting of a 4070A virus and a Moloney murine leukemia virus.

6. The method of claim 1 wherein the inhibitory protein binds to a receptor present on the outer cell membrane of the target cell.

7. The method of claim 1 wherein the candidate polynucleotides are obtained from a cell which is likely to express a protease.

8. The method of claim 7 wherein the cell is a tumor cell.

9. The method of claim 7 wherein the cell is obtained from a tissue which is inflamed.

10. The method of claim 7 wherein the cell is obtained from a tissue which is undergoing remodeling.

11. The method of claim 7 wherein the cell comprises an infectious agent which expresses a protease.

12. The method of claim 7 wherein the cell is obtained from a tissue which is involved in wound healing.

13. The method of claim 1 wherein the candidate polynucleotide molecules are synthetic polynucleotides.

14. The method of claim 1 wherein the transferable label is a selectable marker.

15. The method of claim 14 wherein the selectable marker is an antibiotic resistance gene.

16. The method of claim 1 wherein the candidate polynucleotide molecules comprise primers for amplifying the candidate polynucleotide molecules.

17. The method of claim 1, further comprising the step of amplifying the candidate polynucleotide molecule which encodes the protease.

18. The method of claim 17, further comprising the step of sequencing the amplified candidate polynucleotide molecule.

19. The method of claim 1 wherein the inhibitory protein is a CD40 ligand.

20. The method of claim 1 wherein the inhibitory protein is a leucine zipper polypeptide.

21. The method of claim 20 wherein the leucine zipper polypeptide is selected from the group consisting of GCN4, C/EBP, Fos, Jun, and c-myc.

22. The method of claim 1 wherein the inhibitory protein is selected from the group consisting of CD3 antigen, epidermal growth factor, stem cell factor, and insulin-like growth factor I.

23. The method of claim 1 wherein candidate polynucleotides are present in an expression cassette.

24. The method of claim 1 wherein the target cell is selected from the group consisting of a tumor cell, a cell of a tissue which is inflamed, a cell of a tissue which is undergoing remodeling, a cell of a tissue which is involved in wound healing, and a cell which comprises an infectious agent.

25. The method of claim 1 wherein the target cell is subjected to a treatment to modulate protease activity.

26. The method of claim 25 wherein said treatment comprises contacting said target cell with a protease-modulating compound, growth factor, or protease.

27. The method of claim 1 wherein candidate polynucleotides are obtained from a cell which is not known to express a protease.

28. The method of claim 1 wherein candidate polynucleotides are obtained from a cell which is known to express a protease.

29. The method of claim 1 wherein candidate polynucleotides are obtained from a cDNA library.

30. The method of claim 1 wherein candidate polynucleotides encode a mutated version of a known protease.

31. A method of identifying a candidate polynucleotide molecule encoding a cell surface protease or a secreted protease, comprising the steps of:
   (a) contacting viral display packages with target cells, wherein:
      (1) the viral display packages comprise a transferable label and display recombinant envelope proteins in which a protease recognition site has been substituted for a furin cleavage site located between a large glycoprotein subunit of the envelope protein and a transmembrane component of the envelope protein; and
      (2) the target cells comprise expressible candidate polynucleotide molecules, wherein the expressible candidate polynucleotide molecules may or may not encode a protease; and
   (b) detecting a target cell which comprises the transferable label, wherein infection of a target cell by a viral display package occurs only if a protease produced in the target cell activates the envelope protein by cleaving it at the protease recognition site between the large glycoprotein subunit and the transmembrane component.

32. The method of claim 31 further comprising the step of introducing a plurality of candidate polynucleotides into a population of target cells, wherein the plurality of candidate polynucleotides comprises candidate polynucleotides expressible in the target cells.

33. The method of claim 31 wherein the recombinant envelope protein is derived from a viral envelope protein selected from the group consisting of a Moloney murine leukemia virus envelope protein and an influenza virus envelope protein.

34. The method of claim 31 wherein the candidate polynucleotides are obtained from a cell which is likely to express a protease.

35. The method of claim 33 wherein the cell is a tumor cell.

36. The method of claim 33 wherein the cell is obtained from a tissue which is inflamed.

37. The method of claim 33 wherein the cell is obtained from a tissue which is undergoing remodeling.

38. The method of claim 33 wherein the cell comprises an infectious agent which expresses a protease.

39. The method of claim 33 wherein the cell is obtained from a tissue which is involved in wound healing.

40. The method of claim 33 wherein the candidate polynucleotide molecules are synthetic polynucleotides.

41. The method of claim 31 wherein the candidate polynucleotides are obtained from a cDNA library.

42. The method of claim 31 wherein the candidate polynucleotides encode a mutated version of a known protease.

43. The method of claim 31 wherein the candidate polynucleotide molecules comprise primers for amplifying the expressible candidate polynucleotide molecules.

44. The method of claim 43, further comprising the step of amplifying the candidate polynucleotide molecule which encodes the protease.

45. The method of claim 44, further comprising the step of sequencing the amplified candidate polynucleotide molecule.

46. The method of claim 31 wherein candidate polynucleotides are obtained from a cell which is not known to express a protease.

47. The method of claim 31 wherein candidate polynucleotides are obtained from a cell which is known to express a protease.

48. The method of claim 31, wherein the transferable label is a selectable marker.

49. The method of claim 48 wherein the selectable marker is selected from the group consisting of a neomycin, puromycin or phleomycin resistance gene.

50. The method of claim 31, wherein the transferable label is a reporter gene.

51. The method of claim 50, wherein the reporter gene is selected form the group consisting of β-galactosidase, luciferase, β-glucuronidase, green fluorescent protein, autofluorescent proteins, blue fluorescent protein, glutathione-S-transferase, horseradish peroxidase and chloramphenicol acetyltransferase genes.

* * * * *